(12) United States Patent
Yepes et al.

(10) Patent No.: US 9,495,513 B2
(45) Date of Patent: Nov. 15, 2016

(54) GPU-BASED FAST DOSE CALCULATOR FOR CANCER THERAPY

(75) Inventors: Pablo P. Yepes, Houston, TX (US); Wayne David Newhauser, Houston, TX (US);
(Continued)

(73) Assignees: William Marsh Rice University, Houston, TX (US);
(Continued)

( * ) Notice: Subject to any disclaimer, the term of this patent is extended or adjusted under 35 U.S.C. 154(b) by 800 days.

(21) Appl. No.: 13/822,734

(22) PCT Filed: Sep. 16, 2011

(86) PCT No.: PCT/US2011/051955
§ 371 (c)(1),
(2), (4) Date: Oct. 18, 2013

(87) PCT Pub. No.: WO2012/037472
PCT Pub. Date: Mar. 22, 2012

(65) Prior Publication Data
US 2014/0032185 A1 Jan. 30, 2014

Related U.S. Application Data

(60) Provisional application No. 61/384,134, filed on Sep. 17, 2010.

(51) Int. Cl.
*G06F 7/60* (2006.01)
*G06F 17/10* (2006.01)
(Continued)

(52) U.S. Cl.
CPC ......... *G06F 19/3437* (2013.01); *A61N 5/1031* (2013.01); *A61B 6/032* (2013.01)

(58) Field of Classification Search
CPC .................. A61B 6/032; A61N 5/1031; G06F 19/3437
(Continued)

(56) References Cited

U.S. PATENT DOCUMENTS 6,148,272 A 11/2000 Bergstrom et al.
6,714,620 B2 * 3/2004 Caflisch ................. A61N 5/103
378/65
(Continued)

FOREIGN PATENT DOCUMENTS

WO 2009/137794 A2 11/2009

OTHER PUBLICATIONS

Yepes, Pablo, Sharmalee Randeniya, Phillip J. Taddei, and Wayne D. Newhauser. "Monte Carlo fast dose calculator for proton radiotherapy: application to a voxelized geometry representing a patient with prostate cancer." Physics in medicine and biology 54, No. 1 (2008): N21.*

(Continued)

*Primary Examiner* — Aniss Chad
(74) *Attorney, Agent, or Firm* — Osha Liang LLP (57) ABSTRACT

The invention relates to a computer readable medium including software instructions, which when executed by a scaling parameters for processor perform a method. The method includes obtaining a first and a second pre-calculated history, wherein the first and the second pre-calculated history corresponds to a first and a second path of particles through a reference material. The method further includes obtaining a first and a second plurality of phase space points and performing a first and a second set of simulations in parallel on a first and a second GPU. Each simulation uses a distinct one of the first and second plurality of phase space points, the geometry information, and the first and second pre-calculated history. The sets of simulations are performed (Continued)

on the GPU's to obtain a set of simulated histories. The method further includes calculating an absorbed dose of energy in the target using the set of simulated histories.

14 Claims, 6 Drawing Sheets

(75) Inventors: John Gordon Eley, Houston, TX (US)

(73) Assignees: Board of Regents, The University of Texas System, Austin, TX (US)

(51) Int. Cl.
| | | |
|---|---|---|
| *G06F 19/00* | (2011.01) | |
| *A61N 5/10* | (2006.01) | |
| *A61B 6/03* | (2006.01) | |

(58) Field of Classification Search
USPC ............................................................ 703/2
See application file for complete search history.

(56) References Cited

U.S. PATENT DOCUMENTS

| | | | | |
|---|---|---|---|---|
| 6,792,073 | B2* | 9/2004 | Deasy | A61N 5/1031 378/64 |
| 8,125,813 | B2* | 2/2012 | Nizin | A61N 5/1031 250/492.1 |
| 8,145,459 | B2* | 3/2012 | Holland | A61N 5/1031 378/65 |
| 8,401,148 | B2* | 3/2013 | Lu | A61N 5/1031 378/65 |
| 8,467,497 | B2* | 6/2013 | Lu | A61N 5/1049 378/65 |
| 2007/0282575 | A1 | 12/2007 | Gossage | |
| 2013/0188856 | A1* | 7/2013 | Adler, Jr. | A61B 6/12 382/132 |
| 2015/0352374 | A1* | 12/2015 | Gattiker | A61N 5/1048 600/1 |

OTHER PUBLICATIONS

Gu, Xuejun, Dongju Choi, Chunhua Men, Hubert Pan, Amitava Majumdar, and Steve B. Jiang. "GPU-based ultra-fast dose calculation using a finite size pencil beam model." Physics in medicine and biology 54, No. 20 (2009): 6287.*

International Preliminary Report on Patentability issued in PCT/US2011/051955 mailed Mar. 19, 2013 (4 pages).

Written Opinion issued in PCT/US2011/051955 mailed Apr. 10, 2013 (3 pages).

International Search Report issued in PCT/US2011/051955 mailed Apr. 10, 2012 (2 pages).

Xun Jia et al.; "Development of a GPU-based Monte Carlo dose calculation code for coupled electron-photon transport"; Physics in Medicine and Biology, 2010, 55(11); pp. 3077-3086; May 12, 2010 (10 pages).

* cited by examiner

GPU-BASED FAST DOSE CALCULATOR FOR CANCER THERAPY

CROSS-REFERENCE TO RELATED APPLICATIONS

This application claims priority pursuant to 35 U.S.C. §119(e) to U.S. Provisional Patent Application No. 61/384,134 entitled "GPU-BASED FAST DOSE CALCULATOR FOR CANCER THERAPY," filed on Sep. 17, 2010, the disclosure of which is incorporated by reference herein in its entirety.

BACKGROUND

There are three major strategies used to treat cancer: surgery, chemotherapy, and radiotherapy. Frequently these modalities are combined to increase tumor control or to reduce treatment side effects. In radiotherapy, there is wide acceptance of the view that considerable benefits could be obtained with a quality increase of treatment plans by reducing the radiation doses to healthy tissues. One important component for the quality of a treatment plan and tumor response is the accuracy of dose calculations. The clinical advantages of more accurate dose calculations (i.e., how the treatment plans with higher quality dose calculations will impact tumor recurrence, local control, and normal tissue complications) has not been fully quantified and requires further investigation. Nevertheless evidence exists that dose differences on the order of 7% are clinically detectable.

Accordingly, accurate calculations that may predict the dose to be delivered to a patient undergoing radiotherapy are important for the planning and administration of a particular treatment.

SUMMARY

In general, in one aspect, the invention relates to a computer readable medium including software instructions, which when executed by a processor perform a method. The method includes obtaining a first pre-calculated history, wherein the first pre-calculated history corresponds to a first path of a particle through a reference material. The method further includes obtaining a first plurality of phase space points and performing a first set of $N_T$ simulations in parallel on a first GPU, wherein each simulation uses a distinct one of the first plurality of phase space points, the geometry information, and the first pre-calculated history, wherein the simulation is performed on the first GPU to obtain a first set of $N_T$ simulated histories. The method further includes obtaining a second pre-calculated history, wherein the second pre-calculated history corresponds to a second path of a particle through the reference material. The method further includes obtaining a second plurality of phase space points, performing a second set of $N_T$ simulations in parallel on a second GPU, wherein each simulation uses a distinct one of the second plurality of phase space points, the geometry information, and the second pre-calculated history, wherein the simulation is performed on the second GPU to obtain a second set of $N_T$ simulated histories. The first set of $N_T$ simulations and the second set of $N_T$ simulations are performed substantially in parallel. The method further includes calculating an absorbed dose of energy in the target using the first set of $N_T$ simulated histories and the second set of $N_T$ simulated histories.

Other aspects of the invention will be apparent from the following description and the appended claims.

DETAILED DESCRIPTION

Specific embodiments of the invention will now be described in detail with reference to the accompanying figures. Like elements in the various figures are denoted by like reference numerals for consistency. Further, the use of "FIG." in the drawings is equivalent to the use of the term "Figure" in the description.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention relate to determining a radiation dose for a target region in an object using a simulation, where the simulation uses GPUs. Further, embodiments of the invention relate to using first principles to calculate length and angle scaling parameters used in the simulation. In addition, embodiments of the invention relate to using photons and/or protons in the simulation.

Figure 1:
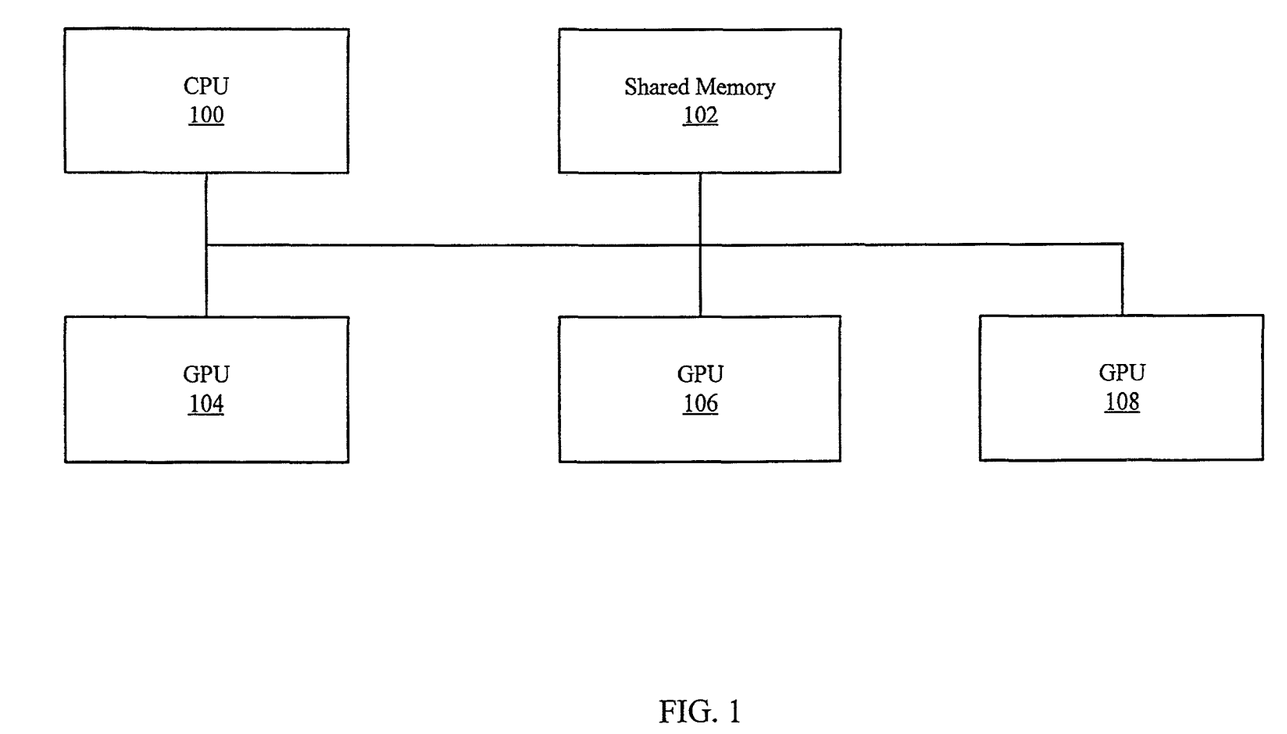
FIG. 1 shows a system in accordance with one or more embodiments of the invention.

FIG. 1 shows a system in accordance with one or more embodiments of the invention. The system includes a CPU (100), shared memory (102), and one or more graphics processing units (GPUs) (104, 106, 108). All of the aforementioned components are operatively connected. Each of the aforementioned is described below.

In one embodiment of the invention, the CPU (100) is a processing unit configured to execute instructions stored on a non-transitory computer readable medium, e.g., the shared memory, other non-transitory computer readable media not shown in FIG. 1. The aforementioned instructions, when executed by the CPU, are configured to manage the execution of a fast dose calculator (FDC) that employs a track-repeating algorithm (TRA) on the GPUs (104, 106, 108). More specifically, in one embodiment of the invention, the instructions, when executed by the CPU, are configured to initiate the execution of threads on the GPUs to perform various calculations (see FIGS. 2-3). The results of the calculations are stored in the shared memory (102). Further, the instructions, when executed by the CPU, are configured to obtain the results of the individual calculations from the GPUs to calculate (or otherwise determine) the simulated radiation dose of the target.

In one embodiment of the invention, the shared memory (102) is memory accessible to the CPU (100) as well as all of the GPUs (104, 106, 108). The shared memory is configured to store simulation results (which may take the form of a plurality of simulated particle histories and/or absorbed energy) on a per-voxel basis. Accordingly, for a given voxel the shared memory may include simulation results for all histories that intersect with the voxel during the simulation (described below) and may also include the energy deposited or absorbed in the voxel during the simulation. The shared memory (102) may be implemented using any type of volatile or non-volatile memory provided that such memory allows for storage and retrieval of simulation results. Further, those skilled in the art will appreciate that while in various embodiments of the invention the shared memory is configured to store simulation results on a per-voxel basis, the shared memory may store simulation results using other schemes without departing from the invention.

In one embodiment of the invention, each GPU is a graphics processing unit configured to perform general purpose scientific and engineering computing. In one embodiment of the invention, each GPU may include two or more multiprocessors. Further, each multiprocessor may include on-chip shared memory, which may be accessed by all threads executing on the multiprocessor. Further, data may be shared between threads executing on different multiprocessors on the GPU using a unified L2 cache. As shown in FIG. 1, the model for GPU computing is to use a CPU and one or more GPUs together in a heterogeneous co-processing computing model. In one embodiment of the invention, the sequential part of the application executes on the CPU and the computationally-intensive part is accelerated by the GPUs. An example of a GPU is NVIDIA's Tesla 20-series GPUs.

In one embodiment of the invention, the target corresponds to a particular portion of a mammal (e.g., a human, a canine, a feline, etc.) that includes a tumor (or a portion of a tumor) (e.g., a cancerous tumor). Furthermore, in accordance with one or more embodiments, the target may correspond to particular components of the particle beam apparatus (e.g., beam shaping components, aperture, range compensator, nozzle, etc).

Figure 2:
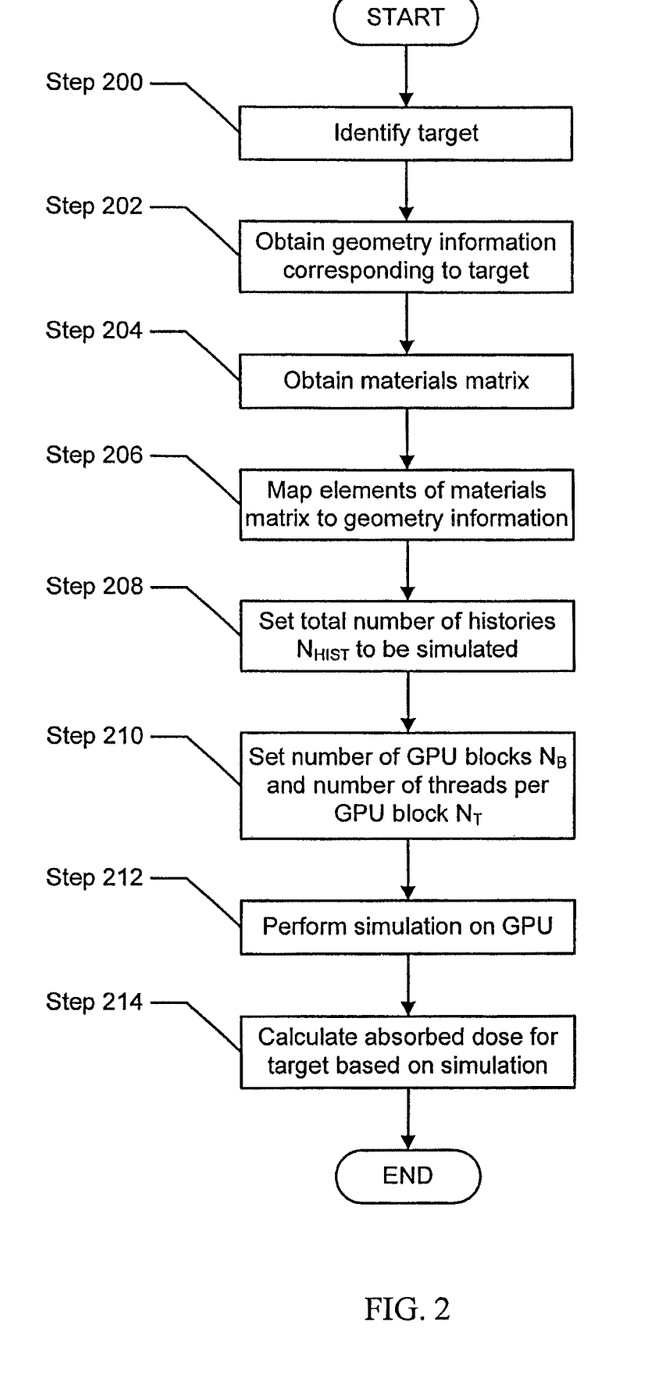
FIG. 2 shows a flowchart in accordance with one or more embodiments of the invention.
Figure 3:
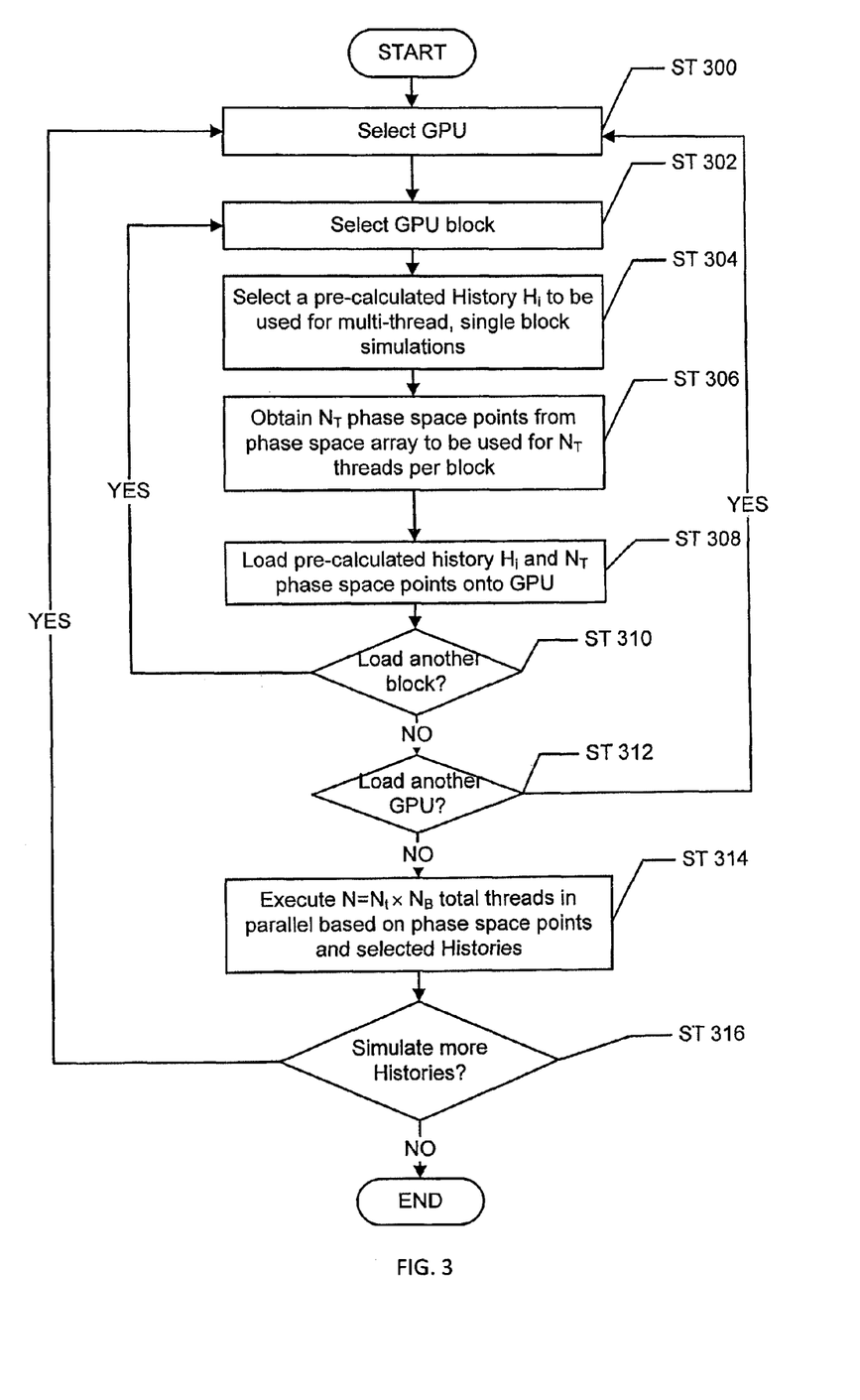
FIG. 3 shows a flowchart in accordance with one or more embodiments of the invention.
Figure 4:
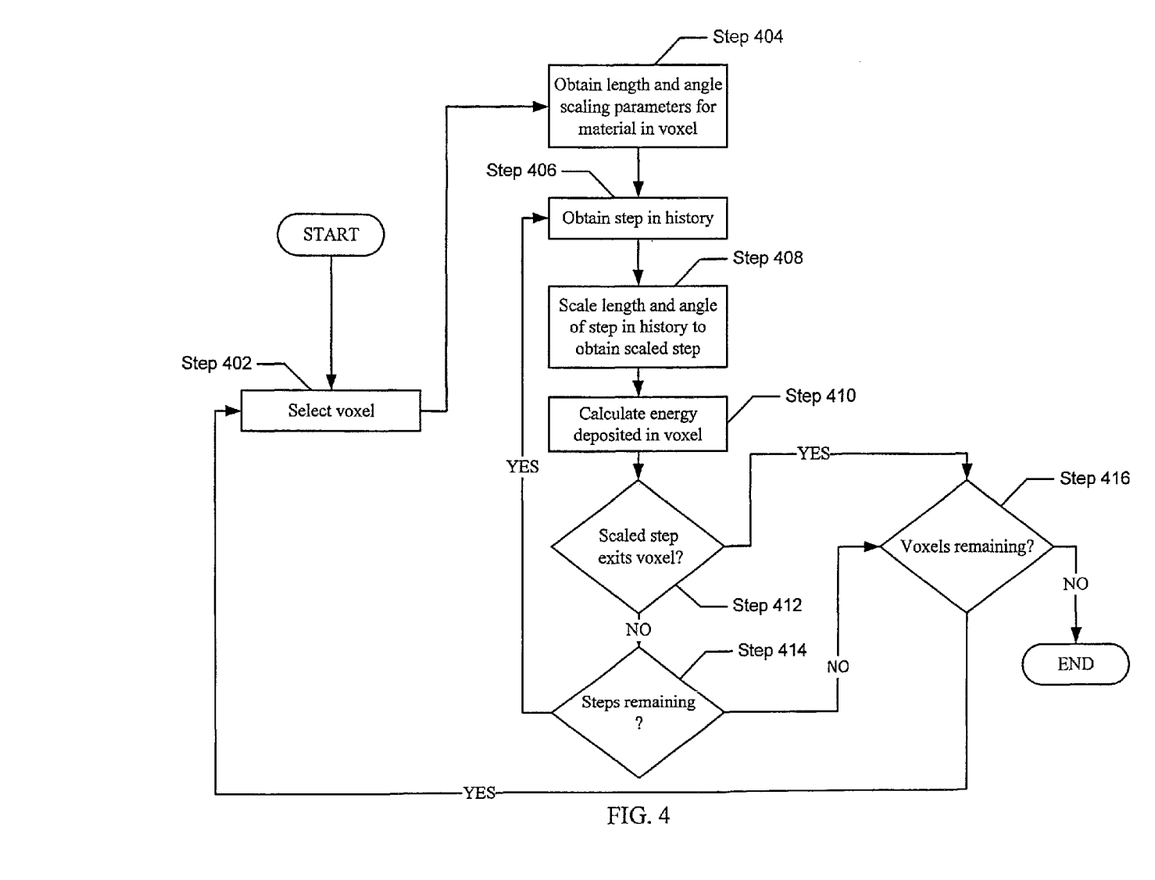
FIG. 4 shows a flowchart in accordance with one or more embodiments of the invention.

FIGS. 2-4 show flowcharts in accordance with one or more embodiments of the invention. While the various steps in the flowcharts shown in FIGS. 2-4 are presented and described sequentially, one of ordinary skill will appreciate that some or all of the steps may be executed in different orders, may be combined, or omitted, and some or all of the steps may be executed in parallel.

FIG. 2 shows a flowchart for executing a simulation in accordance with one or more embodiments of the invention. In step 200, a target to be irradiated is identified. In one embodiment, the target may be a portion of a mammal, e.g., an organ such as a human prostate. In step 202, geometry information corresponding to the target is obtained. In accordance with one or more embodiments of the invention, the geometry information may correspond to a voxellized dataset (known as a phantom) based on images of the actual patient who is to undergo a radiotherapy treatment. In accordance with this embodiment, the voxel is a volumetric picture element, such as a cube or parallelepiped, and a group of voxels corresponding to the target form a three-dimensional (3D) representation of the target. The voxels may be obtained, for example, from a computed tomography (CT) scan of the target. Depending on whether the simulation simulates the irradiation of the target as photons or protons, the voxels obtained from the CT scan may need to be manipulated using techniques known in the art prior to be used in the simulation, e.g., each voxel may be assigned a material composition and density that correspond to the Hounsfield unit value in the CT scan for that voxel. Those skilled in the art will appreciate that the invention is not limited to representing the target using voxels; rather, the target may be represented using any arbitrary geometry without departing from the invention. For example, the target may be represented using surfaces (shells, rings, or other arbitrary shapes that may be convenient according to the natural symmetry of the target).

In step 204, a materials vector is obtained. In accordance with one or more embodiments, the materials vector includes the length scaling and angle scaling parameters for all materials present within the target. The length and/or angle scaling parameters included in the materials vector are nominal scaling parameters that have been calculated in advance for a nominal density in a given material.

In accordance with one or more embodiments, when the radiation includes protons, the length scaling parameters may be determined according to the relation $l=(dE/dx)_{H2O}/(dE/dx)_M$, where $(dE/dx)$ represents energy loss per unit length and M represents a material M (e.g., bone) and H2O represents a water reference material. In accordance with one or more embodiments, the length scaling parameters are determined according to the relation $\sigma_M/\sigma_{H2O}$, where $\sigma_M$ is the root-mean-square (RMS) scattering angle of the particle in a material M and $\sigma_{H2O}$ is the RMS scattering angle in a water reference material.

In one embodiment of the invention, the scaling parameters are numerically determined in advance by simulating histories of photons or protons irradiating a particular material using well-tested Monte Carlo codes, for example, GEANT4 or MCNPX and then performing the same simulation using a Fast Dose Calculator employing a track repeating process (FDC). If there is a difference between the results of the simulation, the length and angle scaling parameters used by the FDC are changed until the difference between the FDC results and the Monte Carlo code results is within an acceptable range. One example of how the scaling parameters may be obtained using the above method is detailed in Yepes, et al., *Phys. Med. Biol.* 54 (2009) N21-N28, which is incorporated by reference in its entirety.

In another embodiment of the invention, the length and/or angle scaling parameters are calculated in advance using first principles. For example, the RMS scattering angle for protons from an incident mono energetic, mono directional, infinitely narrow proton beam passing through a uniform slab of scattering material may be computed with an approximation to the Moliere equation $$\sigma^2 = \frac{\chi^2_{c,eff}}{1+F^2}\left(\frac{1+v_{eff}}{v_{eff}} \ln(1+v_{eff}) - 1\right)(\text{rad}^2)$$

where the effective characteristic angle $\chi_{c,eff}^2$ may be determined for a mixture of elements according to $$\chi^2_{c,eff} = \sum_{i=1}^{N} \chi^2_{c,i}$$

where $$\chi^2_{c,i} = \frac{0.157 z Z_i (Z_i + 1) x_i}{A_i p^2 \beta^2},$$

and

F=0.98, is the fraction of the Moliere angular scattering distribution, $z$=charge of proton, $Z_i$=atomic number of element, $x_i$=fix, $f_i$=fractional mass of element i, x=mass length of scattering material (g/cm$^3$), $A_i$=atomic mass of element i (g/mol), p=momentum of proton (MeV/c)=$\sqrt{(E_k+m_0c^2)^2-(m_0c^2)^2}$, $E_k$=kinetic energy of incident protons, $m_0$=rest mass of proton=938.272 MeV/c$^2$, c=speed of light in vacuum, β=velocity, v of proton (v/c)=$\sqrt{1-(m_0c^2/E_k+m_0c^2)^2}$, $$v_{eff} = \frac{0.5\,\Omega_{eff}}{1-F},$$

$$\Omega_{eff} = \frac{\chi_{c,eff}^2}{\chi_{a,eff}^2}.$$

The effective screening angle $\xi_{a,eff}^2$ for a mixture of elements is given by $$\chi_{a,eff} = \exp\left(\frac{\sum_{i=1}^{N} x_i Z_i(Z_i+1)\ln(\chi_{a,i})/A_i}{\sum_{i=1}^{N} x_i Z_i(Z_i+1)/A_i}\right),$$

and $$\chi_{a,i} = \sqrt{\frac{2.007\times 10^{-5} Z_i^{2/3}[1+3.34(Z_i z\alpha/\beta)^2]}{p^2}},$$

where the fine structure constant α=1/137.

Further, in the event that the simulation simulates photons (instead of protons), in one embodiment of the invention, it is assumed that there is no angle scaling required for the photons. However, the length scaling parameter for photons in a material M may be calculated as the ratio of the photon mean free path in water relative to the mean free path in material M. Further, the mean free path in any material may be calculated using 1/$\sigma_T$, where $\sigma_T=\sigma_p+\sigma_C+\sigma_{BH}$ and $\sigma_p$, $\sigma_C$, and $\sigma_{BH}$ are the cross sections for photon conversion, Compton scattering, and gamma conversion, respectively. Those cross sections may be calculated as the inverse of the mean free path for their respective processes. Further, the mean free paths may be obtained in the framework of GEANT4 with the ComputeMeanFreePath for the classes G4PEffectModel, G4KleinNishinaCompton, and G4BetheHeitlerModel. In addition, one may include an angle scaling for photons to further increase the accuracy of the dose calculation. Those skilled in the art will appreciate that in one or more embodiments of the invention, the scaling parameters may be calculated prior to the simulation or during the simulation, without departing from the invention.

In step 206, elements of the materials vector are mapped to the geometry information of the target. For example, the elements of the materials vector may be associated with each voxel of the target, resulting in a length and angle scaling parameter being associated with each voxel of the target according to the voxel medium (e.g., pancreas, liver, brain, bone, muscle, skin, air, titanium, etc.). One of ordinary skill will appreciate that that material density may vary within the same overall material. For, example, femur bone may have a different density than the frontal bone of a skull. For example, for each voxel medium, a specific length and/or angle scaling parameter is calculated by scaling the nominal length and/or scaling parameters according to the ratio of the nominal density to the density of the voxel medium.

In step 208, the total number of histories to be simulated $N_{HIST}$ is set. In one embodiment of the invention, the total number of histories to be simulated corresponds to the total number of particles that are chosen for the simulation. In step 210, the number of GPU blocks $N_B$ and number of threads per GPU block $N_T$ is set. In step 212, the simulation is performed using the CPU and GPUs. More specifically, one GPU thread is assigned to each simulated history. The individual threads execute on the GPUs. In accordance with one or more embodiments, the simulation is grouped into GPU blocks where each block executes $N_T$ simulations in parallel and where each simulation uses the same pre-calculated history (see FIGS. 3 and 4. for additional detail). In one embodiment of the invention, the GPUs may execute over 100,000 threads in parallel.

In step 214, the individual results of the simulation calculated by the GPUs (i.e., the results of the executed threads) are used to calculate the dose absorbed by the target also referred to as simulated radiation dose (hereafter simulated absorbed dose). More specifically, the amount of energy deposited in each voxel is determined by summing the amount of energy deposited by each history that intersected with that particular voxel. In one embodiment of the invention, the simulated absorbed dose is specified as energy/mass of the voxel on a per-voxel basis or on the target as a whole.

FIG. 3 shows a flow chart that illustrates a GPU based FDC process for radiotherapy dose calculation in accordance with one or more embodiments of the invention. In step 300, a GPU is selected. In step 302, a GPU block is selected. A GPU block corresponds to a logical grouping of threads, where all threads within a GPU block execute on the same GPU. In one embodiment of the invention, a single GPU may support multiple GPU blocks. The number of threads in a given GPU block may be limited by the GPU. In one embodiment of the invention, the CPU (100) is configured to execute a driver to enable communication with the GPUs. In one embodiment of the invention, the driver and, optionally, hardware on the individual GPUs may include functionality to determine which GPU blocks to execute on which GPUs.

Continuing with FIG. 3, in step 304, a pre-calculated history $H_i$ is selected. In one embodiment of the invention, each pre-calculated history corresponds to a path with two or more steps through a reference material, where each step includes a length, an angle, and an energy loss. (see FIGS. 5 and 6). In another embodiment of the invention, each pre-calculated history is associated with an initial energy.

In accordance with one or more embodiments of the invention, the pre-calculated history may be selected from a database of pre-calculated histories. For example, in the case of proton radiotherapy, the database of pre-calculated proton histories is generated in advance using the GEANT4 tool kit, or other known Monte Carlo codes, in accordance with methods known in the art. The details of this calculation may be found in Yepes, et al., *Phys. Med. Biol.* 55 (2010) 7107-7120, incorporated by reference in its entirety. In one example, the database of pre-calculated histories may be generated by simulating a large number of particle histories through a reference material such as water. For example, particle histories may be generated by simulating a large number (e.g., 100,000) 121 MeV protons impinging on a water reference material. In another example, a particle history may be generated by simulating a large number (e.g., 100,000) of photons with arbitrary energies impinging on a water reference material One of ordinary skill will appreciate that using the appropriate physical models, many different types of particles may be simulated to generate the pre-calculated histories, e.g., photons, protons, neutrons, etc.

Returning to FIG. 3, in step 306, $N_T$ phase space points are obtained from a phase space array. In accordance with one or more embodiments, the phase space array may include an array populated with incident energies, incident directions, incident positions, and/or incident particle species (e.g., proton, photon, etc.). For example, in the case of proton radiotherapy, the phase space array may be populated with a range of randomly chosen incident positions (the range chosen such that the position varies about the central position of the simulated proton beam in a range that accurately describes the width of the real beam that is to be used to administer the radiotherapy), fixed incident energy, and fixed incident directions. Alternative radiotherapy treatments, for example, brachytherapy may call for an alternative choice for the phase space array. For example, the choice of random directions or positions may be more appropriate for a radiation source that emits in all directions (e.g., over the full $4\pi$ solid angle). In accordance with one or more embodiments, the $N_T$ phase space points are used for $N_T$ simulations that are to be performed as a group on the selected GPU block.

In step 308, the pre-calculated history $H_i$ and $N_T$ phase space points are loaded onto the selected GPU. In step 310, a determination is made as to whether another GPU block is to be loaded onto the selected GPU. If another GPU block is to be loaded onto the selected GPU, then the process proceeds to step 302; otherwise the process proceeds to step 312. In step 312, a determination is made as to whether another GPU is to be loaded. If another GPU is to be loaded, the process proceeds to step 300, otherwise the process proceeds to step 314. Once the process proceeds to step 314, $N_B$ GPU blocks have each been loaded with one pre-calculated history and $N_T$ phase space points. Alternatively to the sequential process described above, one of ordinary skill will appreciate that certain CPU architectures may allow for the parallel loading GPU's and GPU blocks.

At step 314, $N=N_T \times N_B$ total threads are executed in parallel by the GPU's. In step 316, a determination is made as to whether the total number of simulated histories has been reached. If the total number of simulated histories has not reached $N_{HIST}$, steps 300-314 are executed again. If the total number of simulated histories has reached $N_{HIST}$, the process ends.

It should be noted that in accordance with one or more embodiments, the specific steps shown in FIG. 3 may change depending on the requirements of the specific hardware architecture and/or requirements of a given GPU. Further, as described above, the system is arranged according a heterogeneous co-processing computing model using both CPU's and GPUs. In accordance with one or more embodiments of the invention, one CPU thread may handle each GPU. The number of CPU threads may be defined in advance during initialization of the system, e.g., anytime before step 212 of FIG. 2. Accordingly, as viewed from the perspective of the individual CPU threads, all GPU blocks on a given GPU are loaded during execution of a single CPU thread, i.e., via a single command.

In order to further illustrate the method described in FIGS. 2 and 3, a simplified example is described in detail below. This example is not intended to limit the scope of the invention. In this example, two GPU's are used, GPU1 and GPU2 ($N_{GPU}$=2). In addition, assume that in step 208, $N_B$=4 and $N_T$=3 i.e., the number of GPU blocks is chosen to be 4 and the number of threads per GPU block is chosen to be 3. Also assume that in step 206, the number of histories to be simulated $N_{HIST}$ is chosen to be 48. One of ordinary skill will appreciate that the above numbers are chosen here to be small in order to provide for a simplified example. In contrast, real-world applications may require simulation of millions of histories. Further, modern graphics cards, such as the GEFORCE GTX 295, manufactured by NVIDIA, may hold 240 GPU cores per GPU. One example of a proof-of-concept application is described within Yepes, et al., *Phys. Med. Biol.* 55 (2010) 7107-7120 wherein $N_B$=500, $N_T$=300 and 184,525 proton histories per second were processed by utilizing two GPU's on the GEFORCE GTX 295. Accordingly, this GPU based processing scheme results in 75.5 increase in the number of proton histories processed per second as compared to existing CPU-based implementations.

Continuing with the example, assume that GPU1 is selected at step 300. Then, at step 302, first GPU block B1 is selected. At step 304, a first pre-calculated history $H_1$ is selected. At step 306 the first three phase space points are selected from the phase space array. At step 308, pre-calculated history $H_1$ along with the first three phase space points are loaded onto GPU1. At step 310, it is determined that another block is to be loaded onto GPU1. Accordingly, a second GPU block B2 is selected at step 302. At step 304, a second pre-calculated history $H_2$ is selected. At step 306 the next three phase space points are selected from the phase space array. At step 308, pre-calculated history $H_2$ along with the selected three phase space points are loaded onto GPU1. At this stage, GPU1 is loaded with data for two GPU blocks (B1, B2), where each GPU block has three phase space points and one pre-calculated history ($H_1$ and $H_2$, respectively), for a total of six phase space points and two pre-calculated histories.

After the second iteration, it is determined at step 310 that no other GPU blocks should be loaded onto GPU1. However, it is determined at step 312 that another GPU is to be loaded. Accordingly, GPU2 is selected at step 300. Then a third GPU block B3 is selected at step 302. At step 304, a third pre-calculated history $H_3$ is selected. At step 306 the next three phase space points are selected from the phase space array. At step 308, pre-calculated history $H_3$ along with the three selected phase space points are loaded onto GPU2. At step 310, it is determined that another GPU block is to be loaded onto GPU2. Accordingly, a fourth GPU block B4 is selected at step 302 and at step 304, a fourth pre-calculated history $H_4$ is selected. At step 306 the next three phase space points are selected from the phase space array. At step 308, pre-calculated history $H_4$ along with the three selected phase space points are loaded onto GPU2. At step 310, it is determined that no additional GPU blocks are to be loaded and in ST 312 it is determined that no additional GPU's are to be loaded. At this stage, data associated with two additional GPU blocks are loaded onto GPU2, each GPU block has three phase space points and one pre-calculated history ($H_3$ and $H_4$, respectively).

Continuing with the example, in step 314, all threads are executed in parallel using the aforementioned data that was loaded onto the GPU's resulting in ($N_{GPU}$=2)×($N_B$=2)×($N_T$=3)=12 total threads, i.e., 12 independent simulations. It should be noted that the 12 simulations are run using only 4 unique pre-calculated histories. However, even though each GPU block uses the same pre-calculated history, each thread uses a unique phase space point. Accordingly, 12 statistically independent simulated histories may be obtained if, for example, the 12 statistically independent phase space points include 12 random initial positions on the target.

In other words, in this example, each pre-calculated history is simulated at three independent incident positions on the target. This method minimizes the logical divergence of the simulations as the threads are executed in parallel on the GPUs. For optimum performance, threads are run in groups so that branches in the code do not impact performance, or put another way, threads of a given group follow the same execution path. For example, using the same pre-calculated history for each GPU block advantageously results in nearly a 50% a decrease in total execution time relative to an arrangement that use 12 unique pre-calculated histories.

Returning to the example, at step 314, it is determined that more histories need to be simulated, i.e., $N_{HIST}$=48 but only 12 histories were simulated in the first iteration of steps 300-316. Accordingly, the above steps 300-316 are performed again to produce 12 more simulated histories (using pre-calculated histories $H_5$-$H_8$). At the end of the simulation, the loop defined by steps 300-316 is performed a total of four times to produce 48 simulated histories.

FIG. 4 shows an example of performing a simulation (i.e., step 316, of FIG. 3) using a FDC process in accordance with one or more embodiments of the present invention. In step 402, a voxel is selected according to the incident position indicated by the selected phase space point. The first pass through step 402 includes selecting the first voxel encountered along the history. Subsequent passes through step 402 correspond to selecting voxels in the path of the history (see FIGS. 5-6). In step 404, the length and angle scaling parameters are obtained for the medium in the selected voxel. Those skilled in the art will appreciate that angle scaling parameters may not be necessary if the simulation is based on photons. However, angular scaling may be used for increased accuracy.

In step 406, a step in the history is obtained. In one embodiment of the invention (e.g., proton simulation), the step in the pre-calculated history that is used in the first pass may be obtained by matching the initial energy of the step to the initial energy of the particle being simulated (as determined by the phase space point). In other embodiments (e.g., photon simulation), the pre-calculated history may have been previously chosen to have a first step that corresponds to the initial energy of the particle being simulated. The first pass through step 406 corresponds to selecting the first obtained step in the history. Subsequent passes through step 406 correspond to selecting the next step in the history. In step 408, the length and angle (if appropriate) scaling parameters are applied to the step (obtained in step 406) to generate a scaled step. (See FIGS. 5-6) In one or more embodiments of the invention, a single step may initially reside in two voxels. In this scenario, the a fractional step is determined from the fraction of the step within the first voxel and the length scaling is applied to this factional step.

In step 410, the energy deposited in the voxel is calculated and the energy of that voxel is updated in memory. In step 412, a determination is made about whether the scaled (or fractionally scaled) step exits the voxel. More specifically, a determination is made about whether the length and trajectory of the scaled step exits a boundary of the voxel (as identified in step 402). If the scaled step does not exit the voxel, the process proceeds to step 414 and a determination is made about whether there are additional steps in the history to simulate. If there are additional steps in the history, the process proceeds to step 406; otherwise the process proceeds to step 416.

In step 416, a determination is made about whether there are any other voxels through which the particle may pass. If there are other voxels through which the particle may pass, the process proceeds to step 402; otherwise the process ends. It should be noted that in the case of where a single step initially resided in two voxels, a new step need not be obtained in step 406. Rather, the remaining fractional step is used.

In accordance with one or more embodiments, the energy deposited in the voxel may be calculated as above but may also include the energy deposition related to the secondary particles.

Furthermore, the absorbed dose may be calculated and stored by adding the calculated energies deposited in all the voxels after the simulation is complete. Alternatively, absorbed dose may be analyzed on a per voxel, or even a per history basis.

Figure 5:
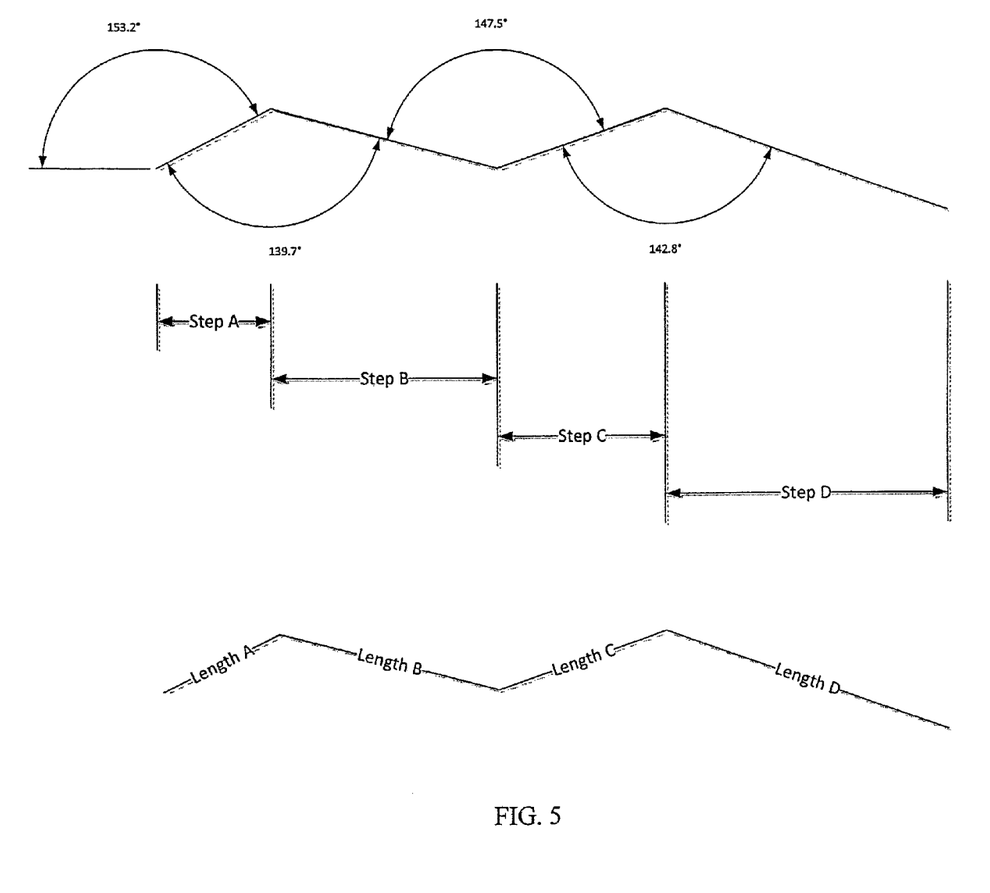
FIG. 5 show an example of a pre-calculated particle history in accordance with one or more embodiments of the invention.
Figure 6:
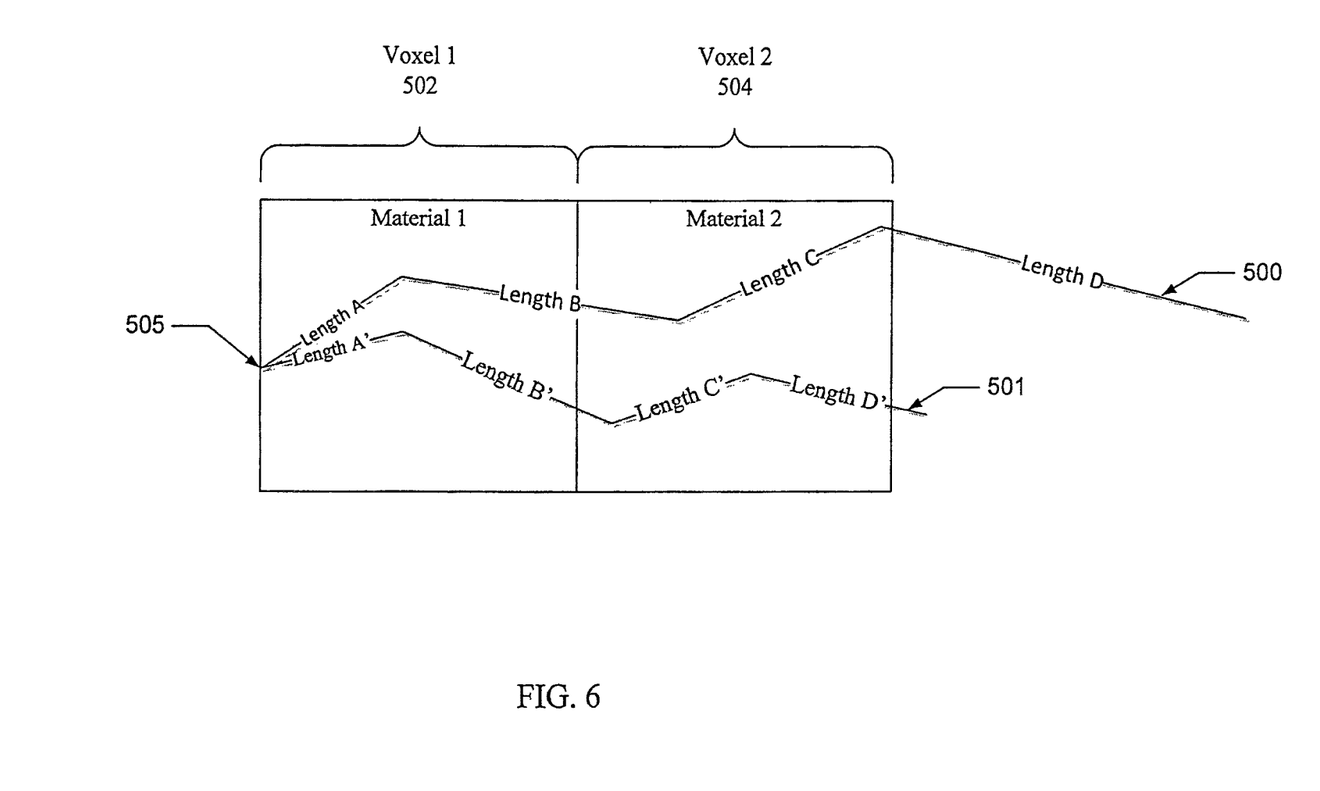
FIG. 6 shows an example of a simulated particle history in accordance with one or more embodiments of the invention.

FIGS. 5-6 show an example in accordance with one or more embodiments of the invention. The example is not intended to limit the scope of the invention.

Referring to FIG. 5, the pre-calculated history includes four steps (step A-D), where each step includes a length (length A-D), and an angle describing the trajectory of the step in relation to the previous step or an initial frame of reference (e.g., 0 degrees) if the step is the initial step in the pre-calculated history. Those skilled in the art will appreciate that while the pre-calculated history is shown as a two-dimensional path, the pre-calculated history is defined on a path traversing three-dimensional space. Accordingly, the angle between the steps may be reflected as two angles: an azimuthal angle and a polar angle. Furthermore, a pre-calculated history may be much more complicated than that shown here. For example, a pre-calculated history may additionally track many secondary, or daughter, particles that are generated at different points in the parent particle's history.

Referring to FIG. 6, a pre-calculated history (500) and a simulated history (501) of a proton traversing two voxels (502, 504) is shown. The following describes the process by which a pre-calculated history is tracked through the sample resulting in a simulated history (501). The simulation is initiated at an initial position (505) that corresponds to the selected phase space point and at the appropriate step in the pre-calculated history. In one embodiment of the invention, the initial step to be simulated is determined based on the energy associated with the phase space point. (See, discussion above in relation to FIG. 3). In FIG. 6, the first step of pre-calculated history (500) begins at initial position 505. Alternative initial conditions are possible based on the values of the phase space array, e.g., a different initial position, a different initial direction, a different initial energy. Initially, voxel 1 (502) is identified and the material for the voxel 1 (502) is determined to be material 1. Based on this information, step A is scaled to obtain scaled step A with length A' as well as a scaled angle. Because scaled step A does not exit voxel 1 (502), step B is obtained and subsequently scaled to obtain scaled step B with length B' as well as a scaled angle. Because scaled step B exits voxel 1 (502), the energy deposited in voxel 1 (502) may be calculated as the sum of (i) the energy deposited in step A and (ii) the energy deposited in step B multiplied by the fraction of step B in voxel 1.

Similarly, when scaled step B enters voxel 2 (504), scaled step B may be further scaled based on the different material i.e., material 2 in voxel 2 (504). As shown in FIG. 6, because scaled step B (which is re-scaled based on material 2 in voxel 2), does not exit voxel 2 (504), the aforementioned scaling process is repeated for step C, and further, for step D. The energy deposited in voxel 2 (504) may be calculated as the sum of (i) the energy deposited in step B multiplied by the fraction of step B in voxel 2; (ii) the energy deposited in step C; and (iii) the energy deposited in step D multiplied by the fraction of step D in voxel 2. Finally, because there are no additional voxels for the proton to pass through, the simulation ends.

Embodiments of the invention may be implemented on virtually any type of computer regardless of the platform being used (with or without a GPU or being operatively connected to one or more GPUs). For example, though not shown, the computer system may include one or more processor(s) such as an integrated circuit, central processing unit or other hardware processor, associated memory (e.g., random access memory (RAM), cache memory, flash memory, etc.), a storage device (e.g., a hard disk, an optical drive such as a compact disk drive or digital video disk (DVD) drive, a flash memory stick, etc.), and numerous other elements and functionalities typical of today's computers (not shown). The computer system may also include input means, such as a keyboard a mouse, or a microphone. Further, the computer system may include output means, such as a monitor (e.g., a liquid crystal display (LCD), a plasma display, or cathode ray tube (CRT) monitor). The computer system may be connected to a network (e.g., a local area network (LAN), a wide area network (WAN) such as the Internet, or any other similar type of network) via a network interface connection (not shown). Those skilled in the art will appreciate that many different types of computer systems exist, and the aforementioned input and output means may take other forms. For example, the computer system may be a server system having multiple blades. Generally speaking, the computer system includes at least the minimal processing, input, and/or output means necessary to practice embodiments of the invention.

Software instructions, which when executed by a processor (e.g., a CPU in FIG. 1) or one or more GPUs (104, 106, 108) in FIG. 1) to perform embodiments of the invention may be stored on a non-transitory computer readable storage medium such as a compact disc (CD), a diskette, a tape, or any other non-transitory computer readable storage medium.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A non-transitory computer readable storage medium comprising software instructions, which when executed by a processor perform a method, the method comprising:
    obtaining geometry information for a target;
    obtaining a first pre-calculated history, wherein the first pre-calculated history corresponds to a first path of a particle through a reference material;
    obtaining a first plurality of phase space points;
    performing a first set of $N_T$ simulations in parallel on a first GPU, wherein each simulation uses a distinct one of the first plurality of phase space points, the geometry information, and the first pre-calculated history, wherein the simulation is performed on the first GPU to obtain a first set of $N_T$ simulated histories;
    obtaining a second pre-calculated history, wherein the second pre-calculated history corresponds to a second path of a particle through the reference material;
    obtaining a second plurality of phase space points;
    performing a second set of $N_T$ simulations in parallel on a second GPU, wherein each simulation uses a distinct one of the second plurality of phase space points, the geometry information, and the second pre-calculated history, wherein the simulation is performed on the second GPU to obtain a second set of $N_T$ simulated histories, wherein the first set of $N_T$ simulations and the second set of $N_T$ simulations are performed substantially in parallel; and
    calculating an absorbed dose of energy in the target using the first set of $N_T$ simulated histories and the second set of $N_T$ simulated histories.

2. The non-transitory computer readable storage of claim 1, wherein each of the plurality of phase space points comprises at least one of selected from a group consisting of an energy, direction, position, and species.

3. The non-transitory computer readable storage medium of claim 1, wherein performing a first set of $N_T$ simulations comprises using a Fast Dose Calculator simulation.

4. The non-transitory computer readable storage medium of claim 1, wherein the particle is a proton.

5. The non-transitory computer readable storage medium of claim 1, wherein the particle is a photon.

6. The non-transitory computer readable storage medium of claim 1, wherein the target is part of a mammal.

7. The non-transitory computer readable storage medium of claim 1, wherein the geometry information comprises a voxellized dataset that corresponds to a three-dimensional (3D) representation of the target.

8. The non-transitory computer readable storage medium of claim 1, wherein the geometry information comprises information corresponding to a tomographic image of the target.

9. The non-transitory computer readable storage medium of claim 1, wherein performing a simulation of the first set of $N_T$ simulations corresponds to tracking the first re-calculated history through the target to obtain a simulated history using at least one scaling parameter.

10. The non-transitory computer readable storage medium of claim 9, wherein the at least one length scaling parameter is obtained using $(dE/dx)_{H_2O}/(dE/dx)_M$, wherein $(dE/dx)$ represents energy loss and M represents a material.

11. The non-transitory computer readable storage medium of claim 1, wherein the reference material is water.

12. The non-transitory computer readable storage medium of claim 1, wherein performing a simulation of the first set of $N_T$ simulations corresponds to tracking the first re-calculated history through the target to obtain a simulated history using at least one scaling parameter, and wherein the at least one length scaling parameter is obtained using a ratio of a photon mean free path in the reference material relative to a photon mean free path in a material.

13. The non-transitory computer readable storage medium of claim 1, wherein performing a simulation of the first set of $N_T$ simulations corresponds to tracking the first re-calculated history through the target to obtain a simulated history using at least one angle parameter.

14. The non-transitory computer readable storage medium of claim 13, wherein the at least one angle scaling parameter is obtained using a ratio of a root means squared (RMS) scattering angle of a particle in a material to an RMS scattering angle of particle in the reference material.

* * * * *